United States Patent [19]

MacDonald

[11] Patent Number: 5,894,347
[45] Date of Patent: Apr. 13, 1999

[54] FLUORIMETER AND DETECTION METHOD

[75] Inventor: Stuart Gilmour MacDonald, Pultneyville, N.Y.

[73] Assignee: Johnson & Johnson Clinical Diagnostics, Inc., Rochester, N.Y.

[21] Appl. No.: 09/075,700

[22] Filed: May 11, 1998

Related U.S. Application Data

[60] Provisional application No.60/049,789, Jun. 16, 1997.
[51] Int. Cl.[6] ................................................. G01N 21/64
[52] U.S. Cl. ........................ 356/317; 356/417; 250/458.1
[58] Field of Search ........................ 356/317, 318, 356/417; 250/458.1, 459.1, 461.1, 461.2

[56] References Cited

U.S. PATENT DOCUMENTS

| | | | |
|---|---|---|---|
| 4,076,420 | 2/1978 | De Maeyer et al. | 356/73 |
| 4,942,303 | 7/1990 | Kolber et al. | 250/458.1 |
| 5,491,343 | 2/1996 | Brooker | 250/458.1 |

*Primary Examiner*—F. L. Evans
*Attorney, Agent, or Firm*—Dana M. Schmidt

[57] ABSTRACT

A method and fluorimeter for flashing a target at several different levels for detection of fluorescence by a PMT without blinding the PMT at the highest level. Two lamps are provided each of which is powered to flash at two different levels that are staged in energy from the lowest of four to the highest of four levels, and a shutter is provided to close off the PMT from exposure when an acceptable, detectable level of fluorescence is detected by the PMT.

4 Claims, 2 Drawing Sheets

1

FLUORIMETER AND DETECTION METHOD

This application is a continuation of Provisional Application No. 60/049,789, filed on Jun. 16, 1997.

FIELD OF THE INVENTION

This invention relates to a flash fluorimeter and method, particularly one useful in detecting PCR-amplified nucleic acid material.

BACKGROUND OF THE INVENTION

Fluorimeters using PMT detectors have been provided in the past, for more or less predictable, minimally varying light levels. In these and all detectors using PMT's, care is required that the light exposure not be so great as to swamp out the upper limit of detectability, since otherwise the PMT either a) takes far too long to "recover", and/or b) is permanently damaged. However, when the light level is not expected to vary much, or is based on a light source emitting at a constant output level, the PMT is not in jeopardy.

A field of use has arisen that does jeopardize the PMT detector. Homogeneous PCR relies in many instances on fluorescence markers whose output is a function of the replicated concentration of the target DNA, which in turn is a function of the starting concentration. As a result, the marker concentration at time of detection can vary by a factor of 100 or more. Stated in other words, usage is possible wherein the fluorophore concentration is much higher than is expected for a given flashlamp intensity, and the PMT is "blinded".

SUMMARY OF THE INVENTION

I have designed a method and a fluorimeter that stage the light output of the flash illuminator so as to start at a very low output, which is increased in intensity until the PMT registers the detection of fluorescence within a certain range. At this point, the increase in flashlamp output is terminated, and the PMT does not risk being overloaded.

More specifically, in accord with a first aspect of the invention, there is provided a fluorimeter useful in detecting a fluorescence signal from PCR-amplified nucleic acid material of unknown concentration, comprising:

- a first and a second light source, at least one of said sources having plural and different levels of intensity, the highest level of intensity of the first source being lower than the lowest level of intensity of the second source;
- means for mounting the light sources orthogonally to each other so as to emit radiation from the first and second sources on first and second paths, respectively, that intersect at a point in space;
- a single beam splitter disposed at the point, the splitter being constructed to transmit at least twice as much light as it reflects;
- means for positioning a test container containing potentially fluorescing sample across the second path;
- a fluorescence signal detector positioned across the second path with the test container, if any, disposed between it and the beam splitter;
- a reference detector positioned across the first path;
- a power source for powering the light sources at their different respective intensities, in sequence from the lowest to the highest of the intensities;
- and switch means for shutting down the power source when a signal is detected by the signal detector greater

2 than a threshold value, even if the highest intensity has not yet been emitted by the second source.

In accord with another aspect of the invention, there is provided a method for detecting a fluorescence signal from PCR-amplified nucleic acid material of unknown concentration, comprising the steps of:

a) flashing a container of said material with a first light flash at a low level and detecting for fluorescence of the material using a PMT detector;

b) if the fluorescence detected in step a) is below a predetermined threshold, then flashing the container with a light flash at a second level greater than the first level while detecting for fluorescence of the material using the PMT detector;

c) if the fluorescence detected in step b) is below the predetermined threshold, then flashing the container with a light flash at additional levels each greater than the previous level while detecting for fluorescence of the material using the PMT detector; and d) during any of the steps a)–c), when a fluorescent signal is detected above the threshold signal, then terminating the flashing of the container so that the PMT detector is protected from over-exposure.

Thus it is an advantageous feature of the invention that a flash fluorimeter is provided that exposes the sample container to a wide range of flash energies for detection of fluorescence by a PMT, without over-exposing the PMT and risking it becoming blinded.

Other advantageous features will become apparent upon reference to the following Detailed Description, when read in light of the attached drawings.

DESCRIPTION OF THE PREFERRED EMBODIMENTS

The following description is of preferred embodiments wherein a particular test container or vessel is described, for use with a flash fluorimeter cycled over a particular time period and at particular, and up to, four energy levels to detect fluorescence produced in amplified nucleic acid material. In addition the invention is useful regardless of the kind of test container used, the time period or levels of energy used in the flash cycle, or the numbers of levels of different flash energy, or the source of the fluorescence detected.

Figure 1:
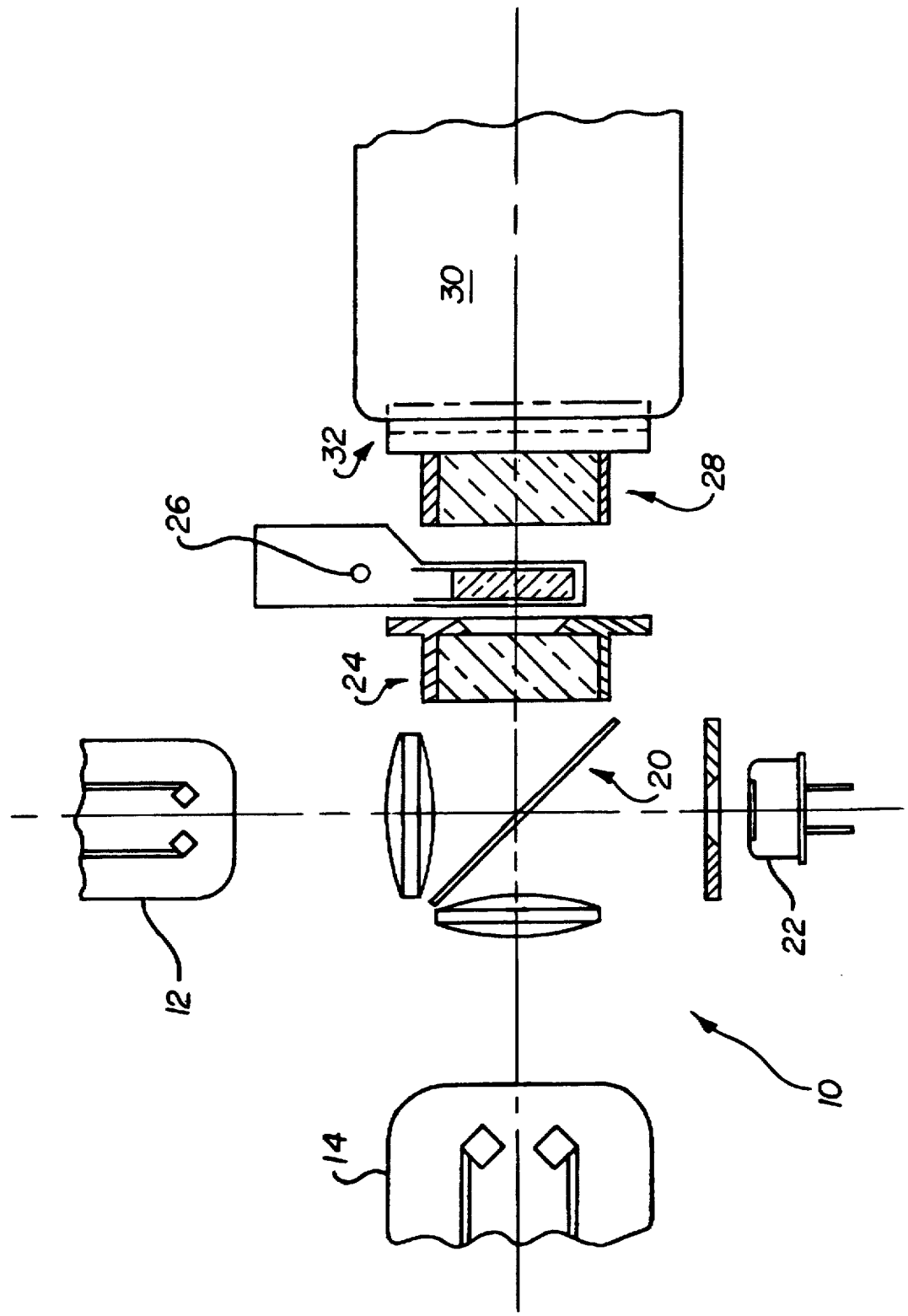
FIG. 1 is a fragmentary, partially schematic view of a fluorimeter constructed in accord with the invention.

In accordance with the invention, such a fluorimeter 10 is constructed, FIG. 1, to have a low-power flashlamp illuminator 12 and a high-power flashlamp illuminator 14, each of which is powered to flash first at a low energy level (for that lamp) and then at a higher level. To keep the levels low and building up gradually, lamp 12 is flashed first at its two levels, and then if needed, lamp 14 is flashed at its lower level, and if needed, then at its higher level. The result is that lamp 12 flashes at a low energy level first, then at a medium energy level, then if needed lamp 14 flashes at a high level, and then at a very high level, all within a 1.5 sec read cycle.

The actual energy levels used for the flashes will of course depend on the amounts of fluorophore targets that are expected in the vessel or test container. Such levels are well within the skill of the skilled artisan. Typically, the energy levels cover a range of from about 0.01 to 10 Joules, each flash occurring for about 4 μseconds.

It will be readily apparent that there is no reason the fluorimeter has to operate at four and only four different energy levels. Lamps can be provided that each operate at, e.g., three levels, for a total of six, or one can be at two levels and one at one or three levels. It all depends on the staging that is expected to be required for the levels of fluorophore that are to be encountered in the test container.

Lamps 12 and 14 are mounted by any suitable means so as to emit radiation orthogonally to each other, as shown, along two respective paths that intersect.

The rest of the fluorimeter comprises a 90/10 beam splitter 20 positioned at the point of intersection of the light paths, a source reference diode detector 22, an excitation filter 24, a test container 26 containing sample with fluorophore markers, an emission filter 28, photomultiplier tube (PMT) detector 30, and shutter 32 that closes whenever detector 30 needs to be protected from ambient light. Surface 34 of the filter 24 acts as the means that positions container 26 across the path of light coming from either lamp.

Figure 2:
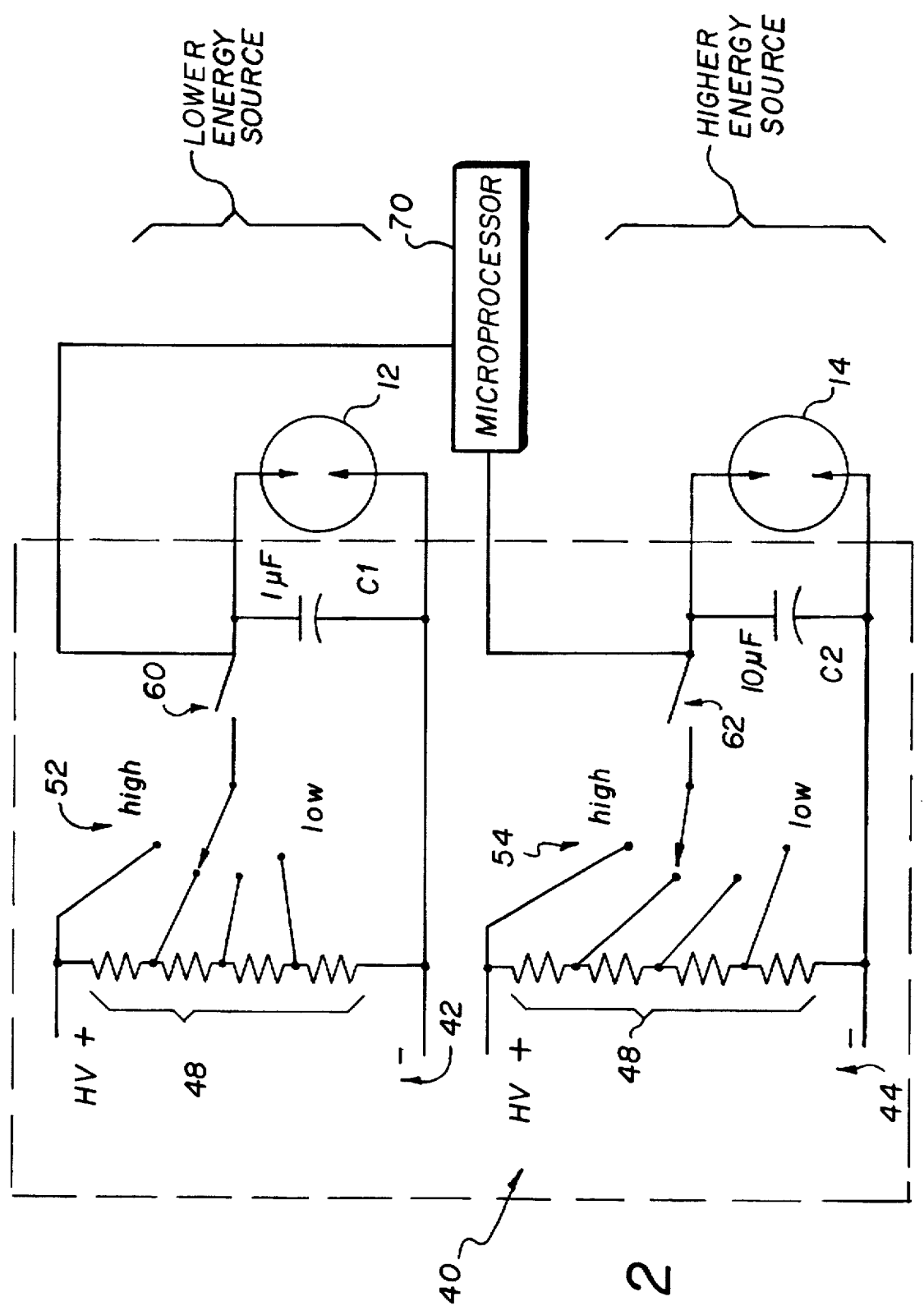
FIG. 2 is a schematic view of a circuit for controlling the powering of the fluorimeter.

A power source 40, FIG. 2, is used to power the lamps at their four different levels, and this can be provided by a variety of conventional equipment. For example, two high voltage sources 42, 44 are separately connected to a stepper switch 52, 54 respectively, which by reason of the voltage divider resistors 48, provide all or a respective fraction of the voltage output of sources 42 or 44. These in turn are connected via switches 60, 62 to the flash lamp 12 and 14, respectively, with capacitors C1 and C2 wired in parallel, C2 having 10× the value of C1. For example, C1 can be 1 microfarad to give a power output of from 0.01 J to 0.1 J, and C2 then is 10 microfarads for an output of 0.1 J to 1.0 J for lamp 14. Switches 60, 62 are controlled, along with the switches 52, 54, by the microprocessor for the fluorimeter, here shown as 70, so that the lamps fire at the proper sequences, and shut off once an adequate signal is detected by detector 30 from the sample container 26.

Useful, detectable fluorophores for homogeneous PCR are described, for example, in *Nature Biotechnology*, Volume 14, March 1996 at Pages 264 and 303–306.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A fluorimeter useful in detecting a fluorescence signal from PCR-amplified nucleic acid material of unknown concentration, comprising:

a first and a second light source, at least one of said sources having plural and different levels of intensity, the highest level of intensity of said first source being lower than the lowest level of intensity of said second source;

means for mounting said light sources orthogonally to each other so as to emit radiation from said first and second sources on first and second paths, respectively, that intersect at a point in space;

a single beam splitter disposed at said point, said splitter being constructed to transmit at least twice as much light as it reflects;

means for positioning a test container containing potentially fluorescing sample across said second path;

a fluorescence signal detector positioned across said second path with said test container, if any, disposed between it and said beam splitter;

a reference detector positioned across said first path;

a power source for powering said light sources at their different respective intensities, in sequence from the lowest to the highest of the intensities; and switch means for shutting down said power source when a signal is detected by said signal detector greater than a threshold value, even if said highest intensity has not yet been emitted by said second source.

2. A fluorimeter as defined in claim 1, wherein said light sources each have two levels of intensity.

3. A method for detecting a fluorescence signal from PCR-amplified nucleic acid material of unknown concentration, comprising the steps of:

a) flashing a container of said material with a first light flash at a low level and detecting for fluorescence of said material using a PMT detector;

b) if the fluorescence detected in step a) is below a predetermined threshold, then flashing said container with a light flash at a second level greater than said first level while detecting for fluorescence of said material using said PMT detector;

c) if the fluorescence detected in step b) is below said predetermined threshold, then flashing said container with a light flash at additional levels each greater than the previous level while detecting for fluorescence of said material using said PMT detector; and d) during any of said steps a)–c), when a fluorescent signal is detected above said threshold signal, then terminating the flashing of said container so that said PMT detector is protected from over-exposure.

4. A method as defined in claim 3, wherein said first and second levels are produced by a first flash lamp, and said additional levels are produced by a second flash lamp.

* * * * *